US007923226B2

(12) United States Patent
Frost

(10) Patent No.: US 7,923,226 B2
(45) Date of Patent: Apr. 12, 2011

(54) SYNTHESIS OF 1,2,4-BUTANETRIOL ENANTIOMERS FROM CARBOHYDRATES

(75) Inventor: John W Frost, Okemos, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 957 days.

(21) Appl. No.: 11/396,177

(22) Filed: Mar. 31, 2006

(65) Prior Publication Data

US 2006/0234363 A1    Oct. 19, 2006

Related U.S. Application Data

(63) Continuation of application No. PCT/US2004/031997, filed on Sep. 30, 2004.

(60) Provisional application No. 60/507,708, filed on Oct. 1, 2003.

(51) Int. Cl.
*C12P 7/18* (2006.01)
*C12N 9/00* (2006.01)
*C12N 1/20* (2006.01)
*C07H 21/04* (2006.01)

(52) U.S. Cl. ............ 435/158; 435/183; 435/252.3; 536/23.2

(58) Field of Classification Search .................. None
See application file for complete search history.

(56) References Cited

U.S. PATENT DOCUMENTS

| | | | |
|---|---|---|---|
| 4,973,769 A | | 11/1990 | Mueller et al. |
| 5,354,574 A | * | 10/1994 | Kobayashi et al. .......... 427/2.13 |
| 5,391,769 A | | 2/1995 | Matsumoto et al. |
| 5,808,107 A | | 9/1998 | Hollingsworth |
| 5,998,633 A | | 12/1999 | Jacks et al. |
| 6,024,810 A | | 2/2000 | Neidert et al. |
| 6,355,848 B1 | | 3/2002 | Antons et al. |
| 6,479,714 B1 | | 11/2002 | Schofield et al. |
| 6,803,501 B2 | | 10/2004 | Baerson et al. |
| 6,858,422 B2 | | 2/2005 | Giver et al. |
| 6,949,684 B2 | | 9/2005 | Ikai et al. |
| 7,008,924 B1 | | 3/2006 | Yan et al. |
| 7,041,805 B2 | | 5/2006 | Baker et al. |
| 7,049,488 B2 | | 5/2006 | Fischer et al. |
| 2003/0233675 A1 | | 12/2003 | Cao et al. |

FOREIGN PATENT DOCUMENTS

| | | |
|---|---|---|
| EP | 1251180 | 10/2002 |
| WO | WO 98/08793 | 3/1998 |
| WO | WO 9938613 | 8/1999 |
| WO | WO 99/44976 | 9/1999 |
| WO | WO 03/106392 | 12/2003 |
| WO | WO 2004/113358 | 12/2004 |
| WO | WO 2005/068642 | 7/2005 |
| WO | WO 2008/091288 | 7/2008 |

OTHER PUBLICATIONS

Niu et al. J Am Chem Soc. Oct. 29, 2003;125(43):12998-9.*
Chica et al. Curr Opin Biotechnol. Aug. 2005;16(4):378-84.*
Sen et al. Appl Biochem Biotechnol. Dec. 2007;143(3):212-23.*
Buchert, J. et al., "Production of xylonic acid by Pseudomonas fragi," Biotechnology Letters, vol. 8, No. 9, pp. 541-546 (1986)—XP008049580.
Huang, Z. & Bao, Y., "Study of continous spraying nitration technique for the mixture of glycerin and 1,2,4-butanetriol," Database Caplus[Online] Chemical Abstracts Service, Columbus, OH, US (1997)—XP-001167027.
Niu, W. et al, "Microbial Synthesis of the Energetic Material Precursor 1,2,4-Butanetriol," Journal of the American Chemical Society, vol. 125, No. 43, pp. 12998-12999 (Oct. 29, 2003)—XP-002335345.
Schimz, K.L. & Kurz, G., "Regulation of L-Arabinose metabolism in Pseudomonas fluorescens," Biochemical Society Transactions, vol. 3, pp. 1087-1089 (1975)—XP008049346.
Tsou, A.Y. et al, "Mandelate Pathway of Pseudomonas putida: Sequence Relationshp Involving Mandelate Racemase, (S)—Mandelate Dehydrogenasse, and Benzoylformate Decarboxylase and Expression of Benzoylformate Decarboxylase in *Escherichia coli*," Biochemistry, vol. 29, No. 42, pp. 9856-9862; abstract, p. 9857, col. 1, line 1, p. 9858, col. 2, line 3, p. 9860 (Oct. 23, 1990)—XP-002335344.
Aoki et al., Identity of dimeric dihydrodiol dehydrogenase as NADP+-dependent D-xylose dehydrogenase in pig liver. Chem. Biol. Inter.130-132, 775-784 (2001).
Asada et al., Roles of His-79 and Tyr-180 of D-xylose/Dihydrodiol Dehydrogenase in Catalytic Function. Biochem. Biophys. Res. Commun. 278, 333-337 (2000).
Brandl et al., Cloning and characterization of a locus encoding an indolepyruvate decarboxylase involved in indole-3-acetic acid synthesis in Erwinia herbicola, Appl. Environ. Microbiol. 62(11), 4121-4128 (1996).
Chain et al., Burkholderia xenovorans LB400 harbors a multi-replicon, 9.73-Mbp genome shaped for versatility. PNAS. 103(42), 15280-15287 (2006).
Conway et al., Promoter and nucleotide sequences of the Zymomonas mobilis pyruvate decarboxylase, J. Bacteriol. 169(3), 949-954 (1987).
Dahms, 3-Deoxy-D-pentulosonic acid aldolase and its role in a new pathway of D-xylose degradation. Biochem. Biophys. Res. Commun. 60(4), 1433-1439 (1974). Database Geneseq [Online], "Bacterial polynucleotide #23683." Retrieved from EBI accession No. GSN:ADT48932. Database accession No. ADT48932. See sequence. (Dec. 2, 2004).
Database UniProt [Online], "RecName: Full=Uncharacterized protein yjhG; EC=<A HREF=" http://srs.ebi.ac.uk/srsbin/cgi-bin/wgetz?[enzyme-ECNumber:4.*.*.*]+-e">4.-.-.-</A; VIMSPQQAKA RGLTSTITFP VGNIAPEGSV IKSTAIDPSM IDEQGIYYHK GVAKVYLSEK". Retrieved from EBI accession No. UNIPROT:P39358. Database accession No. P39358. See sequence. (Feb. 1, 1995).
Database UniProt [Online], "RecName: Full=Uncharacterized protein yagF; EC=<A HREF="http://srs.ebi.ac.uk/srsbin/cgi-bin/wgetz?[enzyme-ECNumber:4.*.*.*]+-e">4.-.-.- </A." Retrieved from EBI accession No. UNIPROT:P77596. Database accession No. P77596. See sequence. (Feb. 1, 1997).
Database UniProt [Online], "RecName: Full=Uncharacterized protein yjhH." Retrieved from EBI accession No. UNIPROT:P39359. Database accession No. P39359. See sequence. (Feb. 1, 1995).

(Continued)

*Primary Examiner* — Christian L Fronda
(74) *Attorney, Agent, or Firm* — Greenberg Traurig, LLP; Jennifer A. Camacho; Fang Xie

(57) ABSTRACT

A bioengineered synthesis scheme for the production of L-1, 2,4-butanetriol, D-1,2,4-butanetriol and racemic mixtures thereof from a carbon source is provided. Methods of producing L-1,2,4-butanetriol, D-1,2,4-butanetriol and racemic mixtures thereof are also provided. Methods are also provided for converting D-1,2,4-butanetriol and L-1,2,4,-butanetriol to D,L-1,2,4-butanetriol trinitrate.

39 Claims, 3 Drawing Sheets

OTHER PUBLICATIONS

Database UniProt [Online], "SubName: Full=Dihydroxy-acid dehydratase; EC=<A HREF="http://srs.ebi.ac.uk/srsbin/cgi-bin/wgetz?[enzyme-ECNumber:4.2.1.9]+-e">4.2.1.9</A>." Retrieved from EBI accession No. UNIPROT:Q5WJ07. Database accession No. Q5WJ07. See sequence. (Nov. 23, 2004).
Database UniProt [Online], "SubName: Full=D-xylose dehydrogenase; EC=<A HREF="http://srs.ebi.ac.uk/srsbin/cgi-bin/wgetz?[enzyme-ECNumber1.1.1.175]+-e">1.1.1.175</A>." Retrieved from EBI assession No. UNIPROT:Q1QWS7. Database assession No. Q1QWS7. See sequence. (May 16, 2006).
Database UniProt [Online], "SubName: Full=D-xylose dehydrogenase; EC=<A HREF="http://srs.ebi.ac.uk/srsbin/cgi-bin/wgetz?[enzyme-ECNumber:1.1.1.175]+-e">1.1.1.175</a>." Retrieved from EBI accession No. UNIPROT:Q13FC8. Database accession No. Q13FC8. See sequence. (Aug. 22, 2006).
Database UniProt [Online], "SubName: Full=Oxidoreductase, short-chain dehydrogenase/reductase family." Retrieved from EBI accession No. UNIPROT:Q9A9ZO. Database accession No. Q9A9ZO. See sequence. (Jun. 1, 2001).
Datsenko et al., One step inactivation of chromosomal genes in *Escherichia coli* K-12 using PCR products. Proc. Natl. Acad. Sci. USA 97, 6640-6645 (2000).
Draths et al., Shikimic acid and quinic acid: replacing isolation from plant sources with recombinant microbial biocatalysis. J. Am. Chem. Soc. 121, 1603-1604 (1999).
Furste et al. Molecular cloning of the plasmid Rp4 primase region in a multi-host-range tacP expression vector. Gene 48, 119-131 (1986).
Hottes et al., Transcriptional profiling of Caulobacter crescentus during growth on complex and minimal media. J. Bacteriol. 186(5), 1448-1461 (2004).

Jensen, Enzyme recruitment in evolution of new function. Ann. Rev. Microbiol. 30, 409-425 (1976).
Johnsen et al., Novel xylose dehydrogenase in the halophilic archaeon Haloarcula marisomortui. J. Bacteriol. 186(18), 6198-6207 (2004).
Jörnvall et al., Short-chain dehydrogenases/reductases (SDR). Biochem. 34(18), 6003-6013 (1995).
Li et al., Fed-batch fermenter synthesis of 3-dehydroshikimic acid using recombinant *Escherichia coli*. Biotechnol. Bioeng. 64(1), 61-73 (1999).
Nierman et al., Complete genome sequence of Caulobacter crescentus. PNAS. 98(7), 4136-4141 (2001).
Perna et al., Genome sequence of enterohaemorrhagic *Escherichia coli* 0157:H7. Nature 409, 529-533 (2001).
Raj et al., Cloning and characterization of the Zymobacter palmae pyruvate decarboxylase gene (pdc) and comparison to bacterial homologues, Appl. Environ. Microbiol. 68(6), 2869-2876 (2002).
Raj et al., Pyruvate decarboxylase: a key enzyme for the oxidative metabolism of lactic acid by Acetobacter pasteurianus, Arch. Microbiol. 176, 443-451 (2001).
Saier et al., Regulation of carbon utilization. In *Escherichia coli* and Salmonella: Cellular and Molecular Biology, edn. 2 (ed. Neidhardt, F.C.) 2118-2202 (ASM Press, Washington, DC 1996).
Schmidt et al., Metabolites: a helping hand for pathway evolution? Trends. Biochem. Sci. 28(6), 336-341 (2003).
Theodossis et al., The structural basis for substrate promiscuity in 2-keto-3-deoxygluconate aldolase from the Entner-Doudoroff pathway in Sulfolobus solfataricus. J. Biol. Chem. 279(42), 43886-43892 (2004).
Weimberg, Pentose oxidation by Pseudomonas fragi. J. Biol. Chem. 236(3), 629-635 (1961).

* cited by examiner

*Reaction conditions: 5000 psi H$_2$, Ru on C, 135 °C, H$_2$O.

US 7,923,226 B2

SYNTHESIS OF 1,2,4-BUTANETRIOL ENANTIOMERS FROM CARBOHYDRATES

RELATED APPLICATIONS

This is a Continuation of PCT Application Ser. No. PCT/US2004/031997, filed Sep. 30, 2004, which claims priority to U.S. Provisional Patent Application Ser. No. 60/507,708, filed Oct. 1, 2003. These Applications are hereby expressly incorporated by reference in their entirety.

SPONSORSHIP

This invention was made with Government support under Contract N00014-00-1-0825, awarded by the Office of Naval Research. The Government may have certain rights in this invention.

INTRODUCTION

The present invention relates to methods of producing microbially synthesized L-1,2,4-butanetriol, D-1,2,4-butanetriol and racemic mixtures thereof. For example, the compositions and methods of this invention comprise the use of the L- and D-1,2,4-butanetriol produced from the microbe as a precursor to the production of D,L-1,2,4-butanetriol trinitrate. See FIG. 1(a).

1,2,4-butanetriol is a chiral polyhydroxyl alcohol with enantiomers D-1,2,4-butanetriol and L-1,2,4-butanetriol. The 1,2,4-butanetriol is useful in energetic compounds. For example, racemic D, L-1,2,4-butanetriol may be nitrated to form the energetic material D,L-1,2,4-butanetriol trinitrate, which is less shock sensitive, more thermally stable and less volatile than nitroglycerin. (*CPIA/M3 Solid Propellant Ingredients Manual*; The Johns Hopkins University, Chemical Propulsion Information Agency: Whiting School of Engineering, Columbia, Md., 2000.) Nitration may be readily performed by use of a variety of commercially available nitrating agents. Common nitrating agents include: $HNO_3$ (or mixtures of $HNO_3$ and $H_2SO_4$), $N_2O_4$ (or mixtures of $N_2O_4$ and $NO_2$), $N_2O_5$ (or mixtures of $N_2O_5$ and $HNO_3$), $NO_2Cl$, peroxynitrite salts ($X^+O\!=\!N\!-\!O\!-\!O^-$, commercially available as, e.g., $Na^+$, $K^+$, $Li^+$, ammonium, or tetraalkylammonium peroxynitrites), and tetranitromethane, and compositions containing one or more such agent. However, substituting D,L-1,2,4-butanetriol trinitrate for nitroglycerin has been impeded by the limited availability of 1,2,4-butanetriol starting materials.

L- and D-1,2,4-butanetriol have previously been obtained at the commercial level by the high pressure catalytic hydrogenation of D,L-malic acid. FIG. 1(b). The reaction employs $NaBH_4$ reduction of esterified D,L-malic acid under high pressure. (U.S. Pat. No. 6,479,714, Monteith, et al., Nov. 12, 2002; PCT Int. Appl. WO 99/44976, Ikai, et al., Sep. 10, 1999.) These synthesis techniques form a variety of byproducts and for each ton of D,L-1,2,4-butanetriol synthesized, multiple tons of byproducts are generated. (Adkins, H.; Billica, H. R. *J. Am. Chem. Soc.* 1948, 70, 3121; Mueller, H.; Mesch, W.; U.S. Pat. No. 4,973,769, Broellos, K., issued Nov. 27, 1990; U.S. Pat. No. 6,355,848, Antons, et al., issued Mar. 12, 2002.) Additionally, the current substitutes for high pressure catalytic hydrogenation of D,L-malic acid used to obtain butanetriol are expensive, have low yields or are generally impractical for large scale use.

It may be desirable to provide an improved method for producing 1,2,4-butanetriol that is cost efficient and uses inexpensive starting materials. It would be further desirable if the method produced good yields of high purity D- and L-1,2,4-butanetriol, minimized byproduct yields and was suitable for commercial and large scale applications.

SUMMARY

The present invention provides methods for producing D-, L-, and D,L-1,2,4-butanetriol comprising the conversion of D-xylose, L-arabinose, or both inside of a transformed host cell, as well as methods for producing D-, L-, and D,L-1,2,4-butanetriol comprising the conversion of D-xylonic acid, L-arabinonic acid, or both inside of a transformed host cell. Microbes comprising enzyme constructs for the synthesis of D-1,2,4-butanetriol and of L-1,2,4-butanetriol, and intermediates are also provided. Methods for converting D,L-1,2,4-butanetriol to D,L-1,2,4-butanetriol trinitrate are also provided.

It has been found that the methods and apparatus of this invention afford benefits over methods and apparatus among those known in the art. Such benefits include reduced production of byproducts from the production of D,L-1,2,4-butanetriol and decreased cost by substituting microbially produced D,L-1,2,4-butanetriol as the precursor for 1,2,4-butanetriol trinitrate for nitroglycerin.

The present invention further provides:

DNA constructs comprising an mdlC gene encoding benzoylformate decarboxylase, an aadh gene encoding L-arabinonate dehydratase, or an aatp gene encoding L-arabinonate transport protein; plasmids comprising the constructs; transformed host cells containing the constructs;

Methods for microbial synthesis of D-1,2,4-butanetriol, comprising (a) inducing a preparation pathway by transforming a host cell with recombinant DNA, and (b) culturing the transformant of step a) in a xylose containing medium;

Such methods further comprising growing the culture with agitation until said cultures appeared turbid; such methods further comprising, transferring the turbid culture to a medium containing an antibiotic and growing said culture until it reaches OD600 of about 1.0 to about 3.0; such methods further comprising transferring the turbid culture as combined with the antibiotic into the fermentation medium, thereby initiating fermentation; and such methods further comprising maintaining a dissolved oxygen content (D.O.) of about 20% of air saturation through a plurality of stages of the fermentations; and D-1,2,4-butanetriol produced thereby;

Processes for making D-xylonic acid, comprising culturing a microbe capable of D-xylose uptake and expressing D-xylose dehydrogenase, and optionally D-xylonolactonase, in the presence of D-xylose;

Processes for making D-3-deoxy-glycero-pentulosonic acid, comprising culturing a microbe expressing D-xylonate dehydratase in the presence of D-xylonic acid, wherein said cell is capable of D-xylonic acid uptake or said D-xylonic acid is intracellularly produced;

Processes for making D-3,4-dihydroxybutanal, comprising culturing a microbe expressing 2-ketoacid decarboxylase in the presence of D-3-deoxy-glycero-pentulosonic acid;

Processes for making D-1,2,4-butanetriol, comprising culturing a microbe expressing dehydrogenase in the presence of D-3,4-dihydroxybutanal;

Processes of making D-1,2,4-butanetriol within a host cell, comprising the steps of:
(a) converting D-xylose to D-xylonic acid;
(b) converting D-xylonic acid to D-3-deoxy-glycero-pentulosonic acid;
(c) converting D-3-deoxy-glycero-pentulosonic acid to D-3,4 dihydroxybutanal; and (d) converting D-3,4-dihydroxybutanal to D-1,2,4-butanetriol;

Such processes, wherein the conversion of D-xylose to D-xylonic acid is conducted in the presence of D-xylose dehydrogenase, and optionally in the presence of D-xylonolactonase;

Such processes, wherein the conversion of D-xylonic acid to D-3-deoxy-glycero-pentulosonic acid is conducted in the presence of D-xylonate dehydratase;

Such processes, wherein the conversion of D-3-deoxy-glycero-pentulosonic acid to D-3,4-dihydroxybutanal is conducted in the presence of 2-ketoacid decarboxylase;

Such processes, wherein the conversion of D-3,4-dihydroxybutanal to D-1,2,4-butanetriol is conducted in the presence of an alcohol dehydrogenase having aldehyde reductase activity, or in the presence of a carbonyl reductase; and D-1,2,4-butanetriol produced thereby;

Methods of preparation of the compound D-1,2,4-butanetriol within a host cell, comprising the steps of:
(a) converting D-xylose to D-xylonic acid with D-xylose dehydrogenase;
(b) converting D-xylonic acid to D-3-deoxy-glycero-pentulosonic acid with D-xylonate dehydratase;
(c) converting D-3-deoxy-glycero-pentulosonic acid to D-3,4-dihydroxybutanal with 2-ketoacid decarboxylase; and
(d) converting D-3,4-dihydroxybutanal to D-1,2,4-butanetriol with dehydrogenase; and D-1,2,4-butanetriol produced thereby;

Methods for microbial synthesis of L-1,2,4-butanetriol, comprising (a) inducing a preparation pathway by transforming a host cell with recombinant DNA, and (b) culturing the transformant of step a) in an arabinose containing medium;

Such methods further comprising growing the culture with agitation until said cultures appeared turbid; such methods further comprising, transferring the turbid culture to a medium containing an antibiotic and growing said culture until it reaches OD600 of about 1.0 to about 3.0; such methods further comprising transferring the turbid culture as combined with the antibiotic into the fermentation medium, thereby initiating fermentation; and such methods further comprising maintaining a D.O. of about 20% of air saturation through a plurality of stages of the fermentations; and D-1,2,4-butanetriol produced thereby; and L-1,2,4-butanetriol produced thereby;

Processes for making L-arabinonic acid, comprising culturing a microbe capable of L-arabinose uptake and expressing L-arabinose dehydrogenase, and optionally L-arabinonolactonase, in the presence of L-arabinose.

Processes for making L-3-deoxy-glycero-pentulosonic acid, comprising culturing a microbe expressing L-arabinonate dehydratase in the presence of L-arabinonic acid.

Processes for making L-3,4-dihydroxybutanal, comprising culturing a microbe expressing 2-ketoacid decarboxylase in the presence of L-3-deoxy-pentulosonic acid.

Processes for making L-1,2,4-butanetriol, comprising culturing a microbe expressing dehydrogenase in the presence of L-3,4-dihydroxybutanal.

Methods of preparation of the compound L-1,2,4-butanetriol within a host cell, comprising the steps of:
(a) converting L-arabinose to L-arabinonic acid;
(b) converting L-arabinonic acid to L-3-deoxy-glycero-pentulosonic acid;
(c) converting L-3-deoxy-glycero-pentulosonic acid to L-3,4-dihydroxybutanal; and
(d) converting L-3,4-dihydroxybutanal to L-1,2,4-butanetriol.

Such methods, wherein the conversion of L-arabinose to L-arabinonic acid is conducted in the presence of L-arabinose dehydrogenase, and optionally in the presence of L-arabinonolactonase; Such methods, wherein the conversion of L-arabinonic acid to L-3-deoxy-glycero-pentulosonic acid is conducted in the presence of L-arabinonate dehydratase; Such methods, wherein the conversion of L-3-deoxy-glycero-pentulosonic acid to L-3,4-dihydroxybutanal is conducted in the presence of 2-ketoacid decarboxylase; and Such methods, wherein the conversion of L-3,4-dihydroxybutanal to L-1,2,4-butanetriol is conducted in the presence of dehydrogenase; and L-1,2,4-butanetriol produced thereby;

Methods of preparation of the compound L-1,2,4-butanetriol within a host cell, comprising the steps of:
(a) converting L-arabinose to L-arabinonic acid with L-arabinose dehydrogenase, and optionally with L-arabinonolactonase;
(b) converting L-arabinonic acid to L-3-deoxy-glycero-pentulosonic acid with L-arabinonate dehydratase;
(c) converting L-3-deoxy-glyceropentulosonic acid to L-3,4-dihydroxybutanal with 2-ketoacid decarboxylase; and
(d) converting L-3,4-dihydroxybutanal to L-1,2,4-butanetriol with dehydrogenase; and L-1,2,4-butanetriol produced thereby;

Methods of making D-1,2,4, butanetriol according to the reaction scheme:

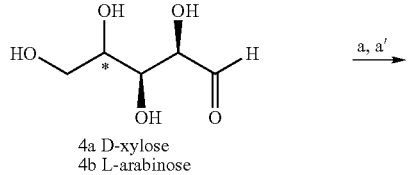

4a D-xylose
4b L-arabinose

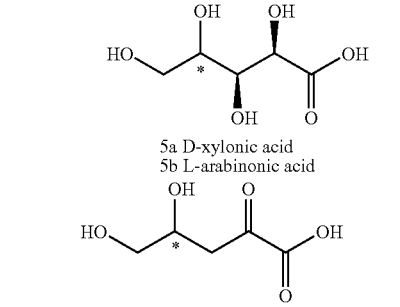

5a D-xylonic acid
5b L-arabinonic acid

6a D-3-deoxy-glycero-pentulosonic acid
6b L-3-deoxy-glycero-pentulosonic acid

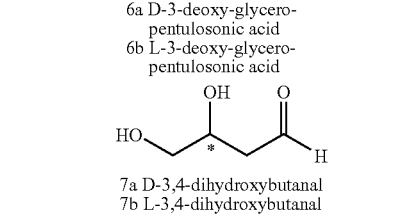

7a D-3,4-dihydroxybutanal
7b L-3,4-dihydroxybutanal

1a D-1,2,4-butanetriol
1b L-1,2,4-butanetriol

Methods of making D,L-1,2,4-butanetriol trinitrate comprising nitration of D,L-1,2,4-butanetriol, wherein the D,L-1,2,4-butanetriol is made by mixing L-1,2,4-butanetriol with D-1,2,4,-butanetriol made by a process according to the present invention;

Methods of making D,L-1,2,4-butanetriol trinitrate comprising nitration of D,L-1,2,4-butanetriol, wherein the D,L-1,2,4-butanetriol is made by mixing D-1,2,4-butanetriol with L-1,2,4,-butanetriol made by a process according to the present invention;

Processes for the production of D-1,2,4-butanetriol from D-xylonic acid, comprising the steps of:
 (a) providing
  (1) D-xylonic acid, and
  (2) a recombinant cell capable of performing uptake of D-xylonic acid, and containing nucleic acid from which the cell can express (a) at least one D-xylonate dehydratase, (b) at least one 2-ketoacid decarboxylase, and (c) at least one alcohol dehydrogenase or carbonyl reductase,
 (b) contacting said cell with said D-xylonic acid under conditions in which the cell uptakes D-xylonic acid and in which the cell expresses, from said nucleic acid, the D-xylonate dehydratase, 2-ketoacid decarboxylase, and alcohol dehydrogenase or carbonyl reductase,
  whereupon said cell
  (c) converts said D-xylonic acid to D-3-deoxy-glyceropentulosonic acid using the D-xylonate dehydratase;
  (d) converts said D-3-deoxy-glyceropentulosonic acid to D-3,4-dihydroxybutanal using the 2-ketoacid decarboxylase; and
  (e) converts said D-3,4-dihydroxybutanal to D-1,2,4-butanetriol using the alcohol dehydrogenase or carbonyl reductase,
  thereby producing D-1,2,4-butanetriol;

Processes for the production of L-1,2,4-butanetriol from L-arabinonic acid, comprising the steps of:
 (a) providing
  (1) L-arabinonic acid, and
  (2) a recombinant cell capable of performing uptake of L-arabinonic acid, and containing nucleic acid from which the cell can express (a) at least one L-arabinonate dehydratase, (b) at least one 2-ketoacid decarboxylase, and (c) at least one alcohol dehydrogenase or carbonyl reductase,
 (b) contacting said cell with said L-arabinonic acid under conditions in which the cell uptakes L-arabinonic acid and in which the cell expresses, from said nucleic acid, the L-arabinonate dehydratase, 2-ketoacid decarboxylase, and alcohol dehydrogenase or carbonyl reductase,
  whereupon said cell
  (c) converts said L-arabinonic acid to L-3-deoxy-glycero-pentulosonic acid using the L-arabinonate dehydratase;
  (d) converts said L-3-deoxy-glycero-pentulosonic acid to L-3,4-dihydroxybutanal using the 2-ketoacid decarboxylase; and
  (e) converts said L-3,4-dihydroxybutanal to L-1,2,4-butanetriol using the alcohol dehydrogenase or carbonyl reductase,
  thereby producing L-1,2,4-butanetriol;

Processes for the production of D-1,2,4-butanetriol from D-xylose, comprising the steps of:
 (a) providing
  (1) D-xylose, and
  (2) a recombinant cell capable of performing uptake of D-xylose, and containing nucleic acid from which the cell can express: (a) at least one D-xylose dehydrogenase and, optionally, at least one D-xylonolactonase; (b) at least one D-xylonate dehydratase; (c) at least one 2-ketoacid decarboxylase; and (d) at least one alcohol dehydrogenase or carbonyl reductase,
 (b) contacting said cell with said D-xylose under conditions in which the cell uptakes D-xylose and in which the cell expresses, from said nucleic acid: the D-xylose dehydrogenase and, optionally, the D-xylonolactonase; the D-xylonate dehydratase; the 2-ketoacid decarboxylase; and the alcohol dehydrogenase or carbonyl reductase,
  whereupon said cell
  (c) converts D-xylose to D-xylonic acid using the D-xylose dehydrogenase, either alone or in combination with the D-xylonolactonase;
  (d) converts said D-xylonic acid to D-3-deoxy-glycero-pentulosonic acid using the D-xylonate dehydratase;
  (e) converts said D-3-deoxy-glycero-pentulosonic acid to D-3,4-dihydroxybutanal using the 2-ketoacid decarboxylase; and
  (f) converts said D-3,4-dihydroxybutanal to D-1,2,4-butanetriol using the alcohol dehydrogenase or carbonyl reductase,
  thereby producing D-1,2,4-butanetriol;

Processes for the production of L-1,2,4-butanetriol from L-arabinose, comprising the steps of:
 (a) providing
  (1) L-arabinose, and
  (2) a recombinant cell capable of performing uptake of L-arabinose, and containing nucleic acid from which the cell can express: (a) at least one L-arabinose dehydrogenase and, optionally, at least one L-arabinonolactonase; (b) at least one L-arabinonate dehydratase; (c) at least one 2-ketoacid decarboxylase; and (d) at least one alcohol dehydrogenase or carbonyl reductase,
 (b) contacting said cell with said L-arabinose under conditions in which the cell uptakes L-arabinose and in which the cell expresses, from said nucleic acid: the L-arabinose dehydrogenase and, optionally, the L-arabinonolactonase; the L-arabinonate dehydratase; the 2-ketoacid decarboxylase; and the alcohol dehydrogenase or carbonyl reductase,
  whereupon said cell
  (c) converts said L-arabinose to L-arabinonic acid using the L-arabinose dehydrogenase, either alone or in combination with the L-arabinonolactonase;
  (d) converts said L-arabinonic acid to L-3-deoxy-glycero-pentulosonic acid using the L-arabinonate dehydratase;
  (e) converts said L-3-deoxy-glycero-pentulosonic acid to L-3,4-dihydroxybutanal using the 2-ketoacid decarboxylase; and
  (f) converts said L-3,4-dihydroxybutanal to L-1,2,4-butanetriol using the alcohol dehydrogenase or carbonyl reductase,
  thereby producing L-1,2,4-butanetriol;

Such processes, wherein at least one of the enzymes is exogenous to the cell;

1,2,4-butanetriol produced thereby;

Non-naturally occurring enzyme systems including at least one D-xylonate dehydratase, at least one 2-ketoacid decarboxylase, and at least one alcohol dehydrogenase or carbonyl reductase, wherein said enzyme system is capable of catalyzing the conversion of D-xylonic acid to D-1,2,4-butanetriol;

Non-naturally occurring enzyme systems including:
 (a) at least one D-xylose dehydrogenase, and optionally at least one D-xylonolactonase, said D-xylose dehydrogenase being capable, either alone or in combination with said D-xylonolactonase, of catalyzing the conversion of D-xylose to D-xylonic acid;
 (b) at least one D-xylonate dehydratase;
 (c) at least one 2-ketoacid decarboxylase; and
 (d) at least one alcohol dehydrogenase or carbonyl reductase,
  wherein said enzyme system is capable of catalyzing the conversion of D-xylose to D-1,2,4-butanetriol;

Non-naturally occurring enzyme systems including at least one L-arabinonate dehydratase, at least one 2-ketoacid decarboxylase, and at least one alcohol dehydrogenase or carbonyl reductase, wherein said enzyme system is capable of catalyzing the conversion of L-arabinonic acid to L-1,2,4-butanetriol;

Non-naturally occurring enzyme systems including:

(a) at least one L-arabinose dehydrogenase, and optionally at least one L-arabinonolactonase, said L-arabinose dehydrogenase being capable, either alone or in combination with said L-arabinonolactonase, of catalyzing the conversion of L-arabinose to L-arabinonic acid;

(b) at least one L-arabinonate dehydratase;

(c) at least one 2-ketoacid decarboxylase; and (d) at least one alcohol dehydrogenase or carbonyl reductase, wherein said enzyme system is capable of catalyzing the conversion of L-arabinose to L-1,2,4-butanetriol;

Such enzyme systems, wherein at least one of the enzymes is a recombinant enzyme; Use of such an enzyme system for the production of 1,2,4-butanetriol; 1,2,4-butanetriol produced by action of such an enzyme system;

Compositions containing such an enzyme system; such compositions which are enzyme bioreactors; such compositions which are dry, frozen, or lyophilized mixtures; such compositions which are aqueous in vitro suspensions or solutions; such compositions which are cellular fermentations in which the cells thereof contain the enzyme system; such compositions which are cell bioreactors in which the cells thereof contain the enzyme system;

Recombinant host cells containing such an enzyme system; such recombinant host cells that have been transformed to be capable of expressing such an enzyme system;

Kits comprising a composition containing such an enzyme system, with instructions for the use thereof for the production 1,2,4-butanetriol; kits comprising nucleic acid encoding such an enzyme system, with instructions for the use thereof for the formation of a recombinant cell capable of producing 1,2,4-butanetriol; kits comprising a composition containing recombinant host cells capable of expressing such an enzyme system, with instructions for the use thereof for the production 1,2,4-butanetriol.

Processes for the preparation of recombinant cells capable of producing 1,2,4-butanetriol from at least one of D-xylose, D-xylonic acid, L-arabinose, or L-arabinonic acid, comprising the steps of:

(a) providing a cell not capable of expressing every one of the enzymes of an enzyme system according to any of claims 68-70, (b) providing nucleic acid from which said cell can express at least one each of the enzyme system enzymes that said cell is otherwise not capable of expressing, (c) transforming the cell with the nucleic acid, thereby forming a recombinant cell capable of producing 1,2,4-butanetriol from D-xylose, D-xylonic acid, L-arabinose, or L-arabinonic acid; and Recombinant cells prepared thereby;

Processes for the production of 1,2,4-butanetriol trinitrate from 1,2,4-butanetriol, comprising the steps of:

(a) providing a nitrating agent, (b) providing, as the 1,2,4-butanetriol, any one of D-1,2,4-butanetriol, D-1,2,4-butanetriol, or D,L-1,2,4-butanetriol, (c) contacting said 1,2,4-butanetriol with said nitrating agent under conditions in which the 1,2,4-butanetriol and the nitrating agent react to form 1,2,4-butanetriol trinitrate, thereby producing 1,2,4-butanetriol trinitrate, wherein said 1,2,4-butanetriol is produced by a process according to the present invention, or is produced by action of an enzyme system according to the present invention; and 1,2,4-butanetriol trinitrate produced thereby;

Compositions containing 1,2,4-butanetriol trinitrate produced thereby; Explosive devices containing 1,2,4-butanetriol trinitrate produced thereby; Methods of blasting or propelling a material object comprising detonating, at a position upon, or adjacent to, a surface of said material object, an explosive device containing 1,2,4-butanetriol trinitrate produced thereby;

1,2,4-butanetriol trinitrate produced from any of D-xylose, D-xylonic acid, L-arabinose, or L-arabinonic acid, or from biosynthetic 1,2,4-butanetriol;

Compositions containing 1,2,4-butanetriol trinitrate produced from any of D-xylose, D-xylonic acid, L-arabinose, or L-arabinonic acid, or from biosynthetic 1,2,4-butanetriol;

Explosive devices containing 1,2,4-butanetriol trinitrate produced from any of D-xylose, D-xylonic acid, L-arabinose, or L-arabinonic acid, or from biosynthetic 1,2,4-butanetriol;

Methods of blasting or propelling a material object comprising detonating, at a position upon, or adjacent to, a surface of said material object, an explosive device containing 1,2,4-butanetriol trinitrate produced from any of D-xylose, D-xylonic acid, L-arabinose, or L-arabinonic acid, or from biosynthetic 1,2,4-butanetriol; and Biosynthetic 1,2,4-butanetriol.

Further benefits and embodiments of the present invention are apparent from the description set forth herein.

FIGURES

Figure 1A:
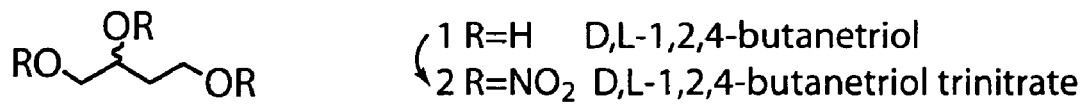
FIG. 1(a) depicts the nitration of D,L-1,2,4-butanetriol to form D,L-1,2,4-butanetriol trinitrate.
Figure 1B:
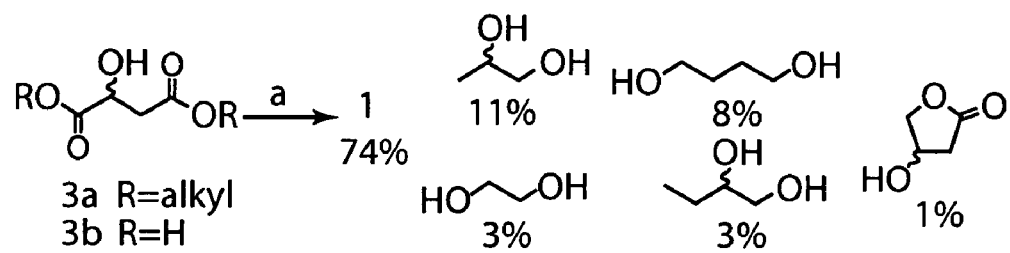
FIG. 1(b) depicts the catalytic hydrogenation of D,L-malic acid.

It should be noted that the figures set forth herein are intended to exemplify the general characteristics of materials and methods among those of this invention, for the purpose of the description of such embodiments herein. These figures may not precisely reflect the characteristics of any given embodiment, and are not necessarily intended to define or limit specific embodiments within the scope of this invention.

DESCRIPTION

The present invention provides bioengineered synthesis methods, materials and organisms for producing D,L-1,2,4-butanetriol and intermediates from a carbon source.

The following definitions and non-limiting guidelines must be considered in reviewing the description of this invention set forth herein. The headings (such as "Introduction" and "Summary,") and sub-headings (such as "Enzyme Assays" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

Classification or discussion of a material within a section of this specification as having a particular utility (e.g., a "catalyst") is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As referred to herein, all compositional percentages are by weight of the total composition, unless otherwise specified.

Figure 2:
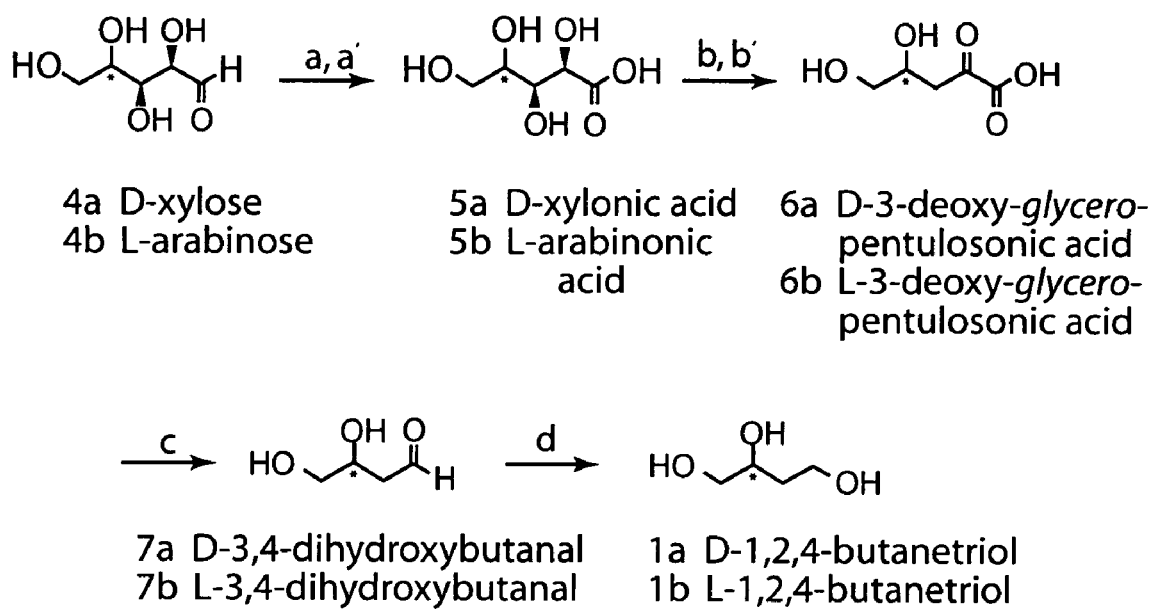
FIG. 2 depicts the conversion of D-xylose and L-arabinose into D-1,2,4-butanetriol and L-1,2,4-butanetriol, respectively.

The bioconversion methods of the present invention are based on the de novo creation of biosynthetic pathways whereby D-1,2,4-butanetriol (1a) and L-1,2,4-butanetriol (1b) are synthesized from a carbon source (FIG. 2). As used herein, the phrase "carbon source" is meant to include biomass-derived carbon sources including, but not limited to, xylose, arabinose, glycerol, glucose and intermediates (e.g., dicarboxylic acids in the Krebs cycle), either alone or in combination. In preferred embodiments, the carbon source is selected from arabinose and xylose, as depicted in FIG. 2 as D-xylose (4a) and L-arabinose (4b).

D-xylose and L-arabinose are the dominant carbohydrates derived from corn fiber and sugar beet pulp. (Salnier, L.; Marot, C.; Chanliaud, E.; Thibault, J.-F. *Carbohydr. Polym.* 1995, 26, 379. Micard, V.; Renard, C. M. G. C.; Thibault, J.-F. *Enzyme Microb. Technol.* 1996, 19, 162.) The opposing C-4 stereogenic centers of D-xylose and L-arabinose, which are the basis for synthesis of D-1,2,4-butanetriol (1a) and L-1,2,4-butanetriol (1b), address the racemic nature of currently employed 1,2,4-butanetriol trinitrate. Microbial synthesis of 1,2,4-butanetriol enantiomers exploit both the abundance and chirality of D-xylose and L-arabinose. As discussed later herein, various methods of the present invention are carried out under conditions of time, temperature, pH, nutrient type and concentration, aeration conditions and carbon source concentrations to provide maximal conversion of the carbon source to D-1,2,4-butanetriol, L-1,2,4-butanetriol and racemic mixtures thereof.

The microbial synthesis of 1,2,4-butanetriol according to embodiments of this invention comprises the substitution of a straightforward enzymatic reduction of an aldehyde for the problematic catalytic reduction of a carboxylic acid known in the art. The reaction conditions associated with high pressure hydrogenation of malic acid are thus avoided and byproduct formation resulting from cleavage of carbon-carbon bonds is also substantially reduced. The significance of such a substitution and the enabling catalytic methodology is considerable given that nitroglycerin has been used in industrial and military energetic materials since the original dynamite formulations developed by Nobel. (Lindner, V. In *Kirk-Othmer Encyclopedia of Chemical Technology*; Kroschwitz, J. I., Howe-Grant, M., Eds.; Wiley: New York, 1993; Vol. 10 p. 46).

In various embodiments, methods of this invention comprise the production of D,L-1,2,4-butanetriol according to the reaction scheme set forth in FIG. 2. While specific details, enzyme sources and mechanisms are provided later herein, it is useful to broadly highlight the reaction pathway. It is understood that discussion of the order or mechanisms of the reaction is not intended to be limiting. First, the carbon sources (4a and 4b) are converted into the corresponding acid (5a and 5b) by dehydrogenases, denoted as a and a', respectively. These acids are then converted to a pentulosonic acids (6a and 6b) by dehydratases, denoted as b and b', respectively. The pentulosonic acids are converted by benzoylformate decarboxylase, denoted as c, into the corresponding aldehydes (7a and 7b). The aldehydes are then converted into the respective butanetriols (1a and 1b) with a dehydrogenase, denoted as d.

Enzymes of the present invention are provided by *Escherichia coli*, preferably *E. coli* K12 or BL21(DE3). Although *E. coli* is specifically described herein as the microbe for carrying out the methods of the present invention, it will be appreciated that any microorganism such as the common types cited in the literature and known to those skilled in the art, may be employed, provided the microorganism can be altered to effect the desired conversion (e.g., carbon source to 1,2,4-butanetriol). Thus it is envisaged that many types of fungi, bacteria and yeasts will work in methods of the present invention. Such microorganisms may be developed, for example, through selection, mutation, and/or genetic transformation processes with the characteristics and necessary capability of converting one constituent of the synthesis scheme of the present invention to another. Methods for such development are well known to the skilled practitioner.

Figure 3:
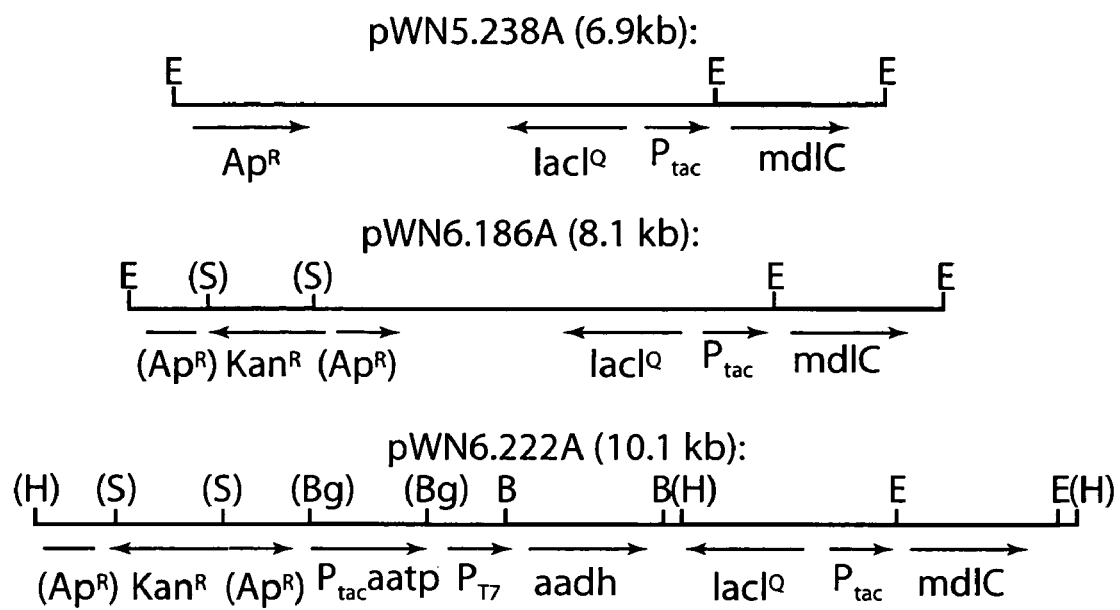
FIG. 3 depicts plasmid restriction enzyme maps for pWN5.238A, pWN6.186A and pWN6.222A.

*E. coli* K12 utilizes D-xylonic acid but not L-arabinonic acid as a source of carbon for growth. Furthermore, native *E. coli* K12 does not contain the pentose dehydrogenases needed to convert the D-xylose and L-arabinose carbon sources into their respective acids, nor the 2-ketoacid decarboxylases needed to produce the respective 3,4-dihydroxybutanal isomers used in the D- and L-1,2,4-butanetriol synthetic pathways. Thus, *E. coli* constructs are employed to provide these absent enzymes. Constructs among those useful herein are depicted in FIG. 3 as the plasmids pWN5.238A (6.9 kb), pWN6.186A (8.1 kb) and pWNN6.222A (10.1 kb). Restriction sites are abbreviated as follows: B corresponds to BamHI, Bg corresponds to BglII, E corresponds to EcoRI, H corresponds to HindIII and S corresponds to ScaI. Parentheses in FIG. 3 indicate that the designated enzyme site has been eliminated. The light face lines indicate vector DNA and bold face lines indicate insert DNA. It is understood that a single or multiple microbes and/or DNA constructs may be employed to provide enzyme activity.

The D-xylose and L-arabinose carbon sources are converted into the conjugate acids, D-xylonic acid and L-arabinonic acid. With respect to D-xylose, *P. fragi* provides the D-xylose dehydrogenase (a) (EC 1.1.1.175) required for conversion to the conjugate acid; in other embodiments, depending on the choice of host cell or in vitro reaction conditions, an NADP-dependent D-xylose dehydrogenase (EC 1.1.1.179) may be used. A D-xylono-1,4-lactonase (EC 3.1.1.68) may also be provided. It is not outside of the scope of this invention to provide the D-xylose dehydrogenase using a D-xylose dehydrogenase from any other source. In an embodiment utilizing L-arabinonic acid, alcohol dehydrogenase activity is the only native *E. coli* enzyme activity recruited for the scheme, although in an in vivo embodiment of a pathway beginning with L-arabinonate in *E. coli*, the host cell is also transformed with a construct providing for expression of an L-arabinonate transport protein. The L-arabinose dehydrogenase (a') (EC 1.1.1.46) is provided using genetic information from *Pseudomonas fragi*. An L-arabinono-1,4-lactonase (EC 3.1.1.15) may also be provided.

The D-xylonic acid and L-arabinonic acid are then converted into the corresponding pentulosonic acids by a dehydratase. In an embodiment utilizing D-xylonic acid, the native *E. coli* enzymes may be used since catabolism of D-xylonic acid coincides with expression of the D-xylonate dehydratase activity required for the generation of 3-deoxy-D-glyceropentulosonic acid (6a). (Dahms, A. S.; Donald, A. *Meth. Enzymol.* 1982, 90, 302.) Recombinant *E. coli* DH5α/pWN6.186A relies on native D-xylonate transport along with native D-xylonate dehydratase (EC 4.2.1.82) and dehydrogenase (i.e. aldehyde reductase) activities. As stated above, a non-native or recombinant source may also be employed to provide the dehydratase and dehydrogenase activity.

With respect to L-arabinonic acid, transformation with recombinant constructs are required in the *E. coli* host cell of the examples, in order to obtain the L-arabinonate dehydratase activity (Weimberg, R. *J. Biol. Chem.* 1959, 234, 727; Achimz, K.-L.; Kurz, G. *Biochem Soc. Trans.* 1975, 3, 1087), which is needed for the formation of 3-deoxy-L-glyceropentulosonic acid (6b). Three separate *P. fragi* cosmids facilitate *E. coli* BL21(DE3)/pWN6.222A use of L-arabinonic acid as a sole source of carbon for growth. An aadh-encoded L-arabinonate dehydratase (EC 4.2.1.25) and an aatp-encoded L-arabinonate transport protein are used which are sourced from a 5.0 kb region shared between the cosmids.

To convert the D- and L-3-deoxy-glycero-pentulosonic acids into the corresponding D- and L-3,4-dihydroxybutanal, recombinant *E. coli* DH5α/pWN6.186A and BL21(DE3)/pWN6.222A, respectively, carry the *P. putida* mdIC plasmid insert encoding benzoylformate decarboxylase. Various microbes may be screened including pyruvate decarboxylases such as *Zymomonas mobilis* (Conway, T.; Osman, Y. A.; Konnan, J. I.; Hoffmann, E. M.; Ingram, L. O. *J. Bacteriol.* 1987, 169, 949), *Acetobacter pasteurianus* (Raj. K. C.; Ingram, L. O.; Maupin-Furlow, J. A. *Arch. Microbiol.* 2001, 176, 443), *Zymobacter palmae* (Raj. K. C.; Talarico, L. A.; Ingram, L. O.; Maupin-Furlow, J. A. *Appl. Environ. Microbiol.* 2002, 68, 2869), and *Saccharomyces cerevisiae*. Other 2-ketoacid decarboxylases may be used (e.g., those of EC 4.1.1.1). Specific examples of other useful 2-ketoacid decarboxylases include benzoylformate decarboxylase (EC 4.1.1.7) expressed by *Pseudomonas putida* (Tsou, A. Y.; Ranson, S. C.; Gerlt, J. A. *Biochem.* 1990 29, 9856) and indole 3-pyruvate decarboxylase (EC 4.1.1.74) expressed by *Erwinia herbicola*. (Brandl, M. T.; Lindow, S. E. *Appl. Environ. Microbiol.* 1996, 62, 4121.) A preferred decarboxylase is benzoylformate decarboxylase.

In various embodiments, native dehydrogenase activity, e.g., primary alcohol dehydrogenase activity, in *E. coli* is adequate for the aerobic reduction of butanal (7a) to D-1,2,4-butanetriol (1a) and butanal (7b) to L-1,2,4-butanetriol (1b) (FIG. 2). In other embodiments, it may be desirable to employ a DNA construct to direct reduction of the butanal to the butanetriol product.

As described later herein, a fermentor cultivation may be used to facilitate conversion of the carbon source to D-1,2,4-butanetriol, L-1,2,4-butanetriol and racemic mixtures thereof. The culture broth may then be nitrated to form the butanetriol-trinitrate from the culture broth. In another embodiment, the butanetriol may be extracted from the culture broth, washed or purified and subsequently nitrated. The fed-batch fermentor process, precipitation methods and purification methods are known to those skilled in the art.

Once formed, the 1,2,4-butanetriol trinitrate may be used as an active ingredient in an energetic (e.g., explosive) composition, which may be in the form of an explosive device. Explosive devices include those designed for use in or as munitions, quarrying, mining, fastening (nailing, riveting), metal welding, demolition, underwater blasting, and fireworks devices; the devices may also be designed or used for other purposes, such as ice-blasting, tree root-blasting, metal shaping, and so forth.

In forming an energetic (e.g., explosive) composition, the 1,2,4-butanetriol trinitrate may be mixed with a further explosive compound, and, alternatively or in addition, with a non-explosive component, such as an inert material, a stabilizer, a plasticizer, or a fuel. Examples of further explosive compounds include, but are not limited to: nitrocellulose, nitrostarch, nitrosugars, nitroglycerin, trinitrotoluene, ammonium nitrate, potassium nitrate, sodium nitrate, trinitrophenylmethylnitramine, pentaerythritol-tetranitrate, cyclotrimethylene-trinitramine, cyclotetramethylene-tetranitramine, mannitol hexanitrate, ammonium picrate, heavy metal azides, and heavy metal fulminates. Further non-explosive components include, but are not limited to: aluminum, fuel oils, waxes, fatty acids, charcoal, graphite, petroleum jelly, sodium chloride, calcium carbonate, silica, and sulfur.

In the examples hereof, native *E. coli* dehydrogenase activity catalyzes the final step of the formation of 1,2,4-butanetriols. Although not wishing to be bound by theory, it is believed that this dehydrogenase activity is effected by one or more primary alcohol dehydrogenases; these are also known as aldehyde reductases. However, any enzymes exhibiting such an aldehyde reductase activity, i.e. that is capable of reducing 3,4,-dihydroxybutanal to 1,2,4-butanetriol, may be substituted. Examples of other enzymes exhibiting useful aldehyde reductase activities include, e.g., primary alcohol dehydrogenases not native to *E. coli*, or not native to the host cell in an in vivo embodiment hereof, and carbonyl reductases. Specific examples of these include NADH-dependent alcohol dehydrogenases (EC 1.1.1.1), NADPH-dependent alcohol dehydrogenases (EC 1.1.1.2), and NADPH-dependent carbonyl reductases (EC 1.1.1.184).

In the examples hereof in which D-xylonic acid is produced in vivo from D-xylose, a *P. fragi* D-xylose dehydrogenase is utilized as the enzyme performing this conversion. While not wishing to be bound by theory, it is believed that this enzyme alone converts D-xylose to D-xylonic acid directly; yet, it is possible that D-xylonolactone (i.e. D-xylono-1,4,-lactone) is formed as a transitory intermediate in this conversion and that a ring-opening step converting the lactone to D-xylonic acid is also being performed. In that case, ring-opening of D-xylonolactone may be performed: by a D-xylonolactonase (i.e. D-xylono-1,4-lactonase) activity also present in the *P. fragi* enzyme; or by a D-xylonolactone ring-opening activity that is native to the host cell, whether this is provided by a chemical or enzymatic entity. As a result, in one embodiment of the present invention, a D-xylonolactonase (EC 3.1.1.68) may also be used in addition to a D-xylose-dehydrogenase. Similarly, an L-arabinonolactonase (i.e. L-arabinono-1,4-lactonase; EC 3.1.1.15) may be used in combination with an L-arabinose dehydrogenase where in vivo conversion of L-arabinose to L-arabinonic acid is desired.

Embodiments of the present invention involve in vivo and in vitro enzymatic pathways. In an in vivo embodiment, at least one of the enzymes will be exogenous to the host cell and will be produced therein as a result of recombinant nucleic acid technology.

A host cell may be capable of uptake of a given compound either because it can absorb the compound by a passive uptake mechanism (e.g., diffusion) or because it can effect an active uptake mechanism (e.g., transport protein-mediated uptake) thereof. In particular, a recombinant host cell of an embodiment of the present invention may utilize either passive or active uptake of, e.g., D-xylose, D-xylonic acid, L-arabinose, and/or L-arabinonic acid. In a preferred embodiment, a recombinant host cell according to the present invention will be capable of active uptake of at least one of D-xylose, D-xylonic acid, L-arabinose, or L-arabinonic acid. In such a preferred embodiment, where the cell selected to be transformed to become a recombinant host cell does not have an active uptake mechanism for the desired compound(s), it will preferably be transformed with nucleic acid it can express to form at least one transport protein capable of use by the cell to achieve active uptake of the desired compound(s).

For example, in one embodiment of in vivo conversion of L-arabinonate to L-1,2,4-butanetriol, in which a cell selected for use therein lacks the ability to activity uptake L-arabinonate, the cell will be transformed with nucleic acid from which it can express an L-arabinonate transport protein that the cell can use to performed active uptake of L-arabinonate. Preferably, the transport protein will be a native or modified form of a transport protein from a cell of the same kingdom as the selected host cell. Thus, a native or modified form of a bacterial L-arabinonate transport protein is preferably used where the selected host cell is a member of the bacteria.

A recombinant host cell capable of 1,2,4-butanetriol production according to an in vivo embodiment of the present invention is one that has been transformed so as to become capable of at least one of: producing D-1,2,4-butanetriol from D-xylose, producing D-1,2,4-butanetriol from D-xylonic acid, producing L-1,2,4-butanetriol from L-arabinose, or producing L-1,2,4-butanetriol from L-arabinonic acid. A recombinant host cell may be capable of producing either or both of L-1,2,4-butanetriol and D-1,2,4-butanetriol. A recombinant host cell capable of producing both of L-1,2,4-butanetriol and D-1,2,4-butanetriol may be used to produce either compound alone, or both compounds simultaneously, depending on the precursor molecules with which it is contacted. Similarly, any in vivo or in vitro enzyme system according to the present invention may be capable of producing either or both 1,2,4-butanetriols, by virtue of containing the enzymes of any one or more of the four pathways, i.e. those: producing D-1,2,4-butanetriol from D-xylose, producing D-1,2,4-butanetriol from D-xylonic acid, producing L-1,2,4-butanetriol from L-arabinose, or producing L-1,2,4-butanetriol from L-arabinonic acid.

In one embodiment, a recombinant host cell hereof is a microbe. In one embodiment, the host cell is a fungal, protist, or prokaryotic cell. In one embodiment, the host cell is a bacterial cell. In one embodiment, the host cell is a proteobacterial cell.

A host cell or enzyme system according to the present invention may be used alone or in combination with a further host cell or enzyme system according to the present invention. In one embodiment, a recombinant host cell capable of producing D-1,2,4-butanetriol, but not L-1,2,4-butanetriol, may be used along with a host cell capable of producing L-1,2,4-butanetriol, but not D-1,2,4-butanetriol, or vice versa, in a mixed cell fermentation or a mixed cell bioreactor.

Moreover, the in vivo or in vitro enzyme systems according to the present invention may be utilized together or in a sequential arrangement. Thus, e.g., in an enzyme bioreactor capable of performing the production of 1,2,4-butanetriol by use of an enzyme system hereof may contain the enzymes located in an interspersed arrangement, or it may contain the enzymes in sequential zones wherein each zone contains one or more than one immediately sequential enzyme in the pathway, but not all enzymes of the pathway, with the zones arranged sequentially according to the order of the reaction pathway.

While the embodiments hereof are illustrated by reference to enzymes, it is understood that one or more or all of such enzymes can be replaced by other types of biocatalysts exhibiting the same activity or activities. Other types of biocatalysts include catalytic nucleic acid molecules, such as RNAzymes (ribozymes) and DNAzymes, and catalytic binding molecules, such as catalytic antibodies (abzymes).

EXAMPLES

Microbial Synthesis of the Energetic Material Precursor 1,2,4-Butanetrio General Chemistry For $^1$H NMR quantification of solute concentrations, solutions are concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-d4 acid (TSP, Lancaster Synthesis Inc., Windham, N.H., USA). Concentrations are determined by comparison of integrals corresponding to each compound with the integral corresponding to TSP ($\delta$=0.0 ppm) in the $^1$H NMR. All $^1$H NMR spectra are recorded on a Varian VXR-500 NMR Spectrometer (500 MHz) (Palo Alto, Calif., USA). Samples analyzed by gas chromatography are derivatized by bis(trimethylsilyl)trifluoroacetamide and quantified relative to an internal standard of dodecane. Gas chromatography is performed on an Agilent 6890N (Palo Alto, Calif., USA) equipped with an HP-5 capillary column (30 m×0.25 mm×0.25 micron). Temperature programming begins with an initial temperature of 120° C. for 3 min. The temperature is increased to 210° C. at a rate of 15° C./min, and held at the final temperature for 1 min. The split injector is maintained at a temperature of 300° C. and the FID detector is kept at 350° C.

High-Pressure Hydrogenation of D,L-Malic Acid

A solution of D,L-malic acid (13.4 g, 0.1 mol) in distilled, deionized water (100 mL) is placed in a glass liner along with 5 wt % Ru on C (2.68 g, 1.33 mmol). The liner is inserted into a 500 mL Parr 4575 stainless steel high temperature, high-pressure reactor (Parr Instrument Co., Moline, Ill., USA) and the vessel sealed. A Parr 4842 controller maintains temperatures and stirring rates. Hydrogen is bubbled through the reaction mixture for 10-15 min to remove air while stirring at 100 rpm. The vessel is then pressurized with 4000 psi $H_2$ (27.6 MPa). After heating the reaction to 135° C., the $H_2$ pressure increased to 5000 psi (34.5 MPa). The reaction is subsequently stirred at 200 rpm for 10 h at 135° C. under 5000 psi $H_2$ (34.5 MPa). After removal of the catalyst by filtration, the reaction mixture is concentrated under vacuum to afford a colorless oil. Individual products in this oil are separated by flash chromatography ($MeOH/CH_2Cl_2$, 1:9, v/v) and identified by $^1H$ NMR as ethylene glycol; 1,2-propanediol; 1,3-butanediol; 1,4-butanediol; 3-hydroxy-δ-butyrolactone and 1,2,4-butanetriol. Product yields are determined by gas chromatography after derivatization. The colorless oil resulting from hydrogenation of D,L-malic acid (~50 mg) is dissolved in pyridine (1 mL, 12.4 mmol) followed by the addition of dodecane (0.1 mL, 0.44 mmol) and bis(trimethylsilyl)trifluoroacetamide (2 mL, 7.53 mmol). The reaction is stirred at room temperature for 3 h and then analyzed by gas chromatography. Based on response factors determined for authentic samples relative to dodecane as the internal standard, product yields resulting from the high-pressure hydrogenation of D,L-malic acid are as follows: ethylene glycol (3%); 1,2-propanediol (11%); 1,3-butanediol (3%); 1,4-butanediol (8%); 3-hydroxy-δ-butyrolactone (1%); 1,2,4-butanetriol (74%).

General Microbiology

All solutions are prepared in distilled, deionized water. LB medium (1 L) contained Bacto tryptone (10 g), Bacto yeast extract (5 g) (Liverpool, NSW, Australia), and NaCl (10 g). LB glucose medium contained glucose (10 g), $MgSO_4$ (0.12 g), and thiamine hydrochloride (0.001 g) in 1 L of LB medium. M9 salts (1 L) contained $Na_2HPO_4$ (6 g), $KH_2PO_4$ (3 g), $NH_4Cl$ (1 g), and NaCl (0.5 g). The M9 D-xylonic acid medium contained potassium D-xylonate (10 g), $MgSO_4$ (0.12 g), and thiamine hydrochloride (0.001 g) in 1 L of M9 salts. M9 L-arabinonic acid medium contained potassium L-arabinonate (10 g), $MgSO_4$ (0.12 g), and thiamine hydrochloride (0.001 g) in 1 L of M9 salts. Except where specifically mentioned, antibiotics are added where appropriate to the following final concentrations: ampicillin (Ap), 50 µg/mL; kanamycin (Kan), 50 µg/mL. Isopropyl-β-D-thiogalactopyranoside (IPTG) is prepared as a 500 mM stock solution. Solutions of LB medium, M9 salts, $MgSO_4$, and glucose are autoclaved individually and then mixed. Solutions of potassium D-xylonate, potassium L-arabinonate, thiamine hydrochloride, antibiotics, and IPTG are sterilized through 0.22-µm membranes. Nutrient agar (Oxoid Inc., Houston, Tex., USA) plates are prepared according to procedure recommended by the manufacture. Other solid media are prepared by addition of Difco agar (Becton Dickinson, Franklin Lakes, N.J., USA) to a final concentration of 1.5% (w/v) to the liquid media. Standard protocols are used for construction, purification, and analysis of plasmid DNA. Sambrook, J. et al., *Molecular Cloning: A Laboratory Manual* (Cold Spring Harbor Laboratory, Plainview, N.Y., 1990). PCR amplifications are carried out as previously described.

Isolation of aadh and aatp Genes

Genomic DNA of *Pseudomonas fragi* (ATCC4973) is isolated according to the procedure described by Wilson. (Wilson, K. In *Current Protocols in Molecular Biology*; Ausubel, F. M.; Brent, R; Kingston, R. E.; Moore, R. E.; Seidman, J. G.; Smith, J. S.; Struhl, K. Eds.; Wiley: NY, 1987.) This DNA is partially digested with Sau3A to afford fragments in the range of 30-42 kb. The resulting DNA fragments are ligated into BamHI-digested cosmid vector SuperCos I (Stratagene, La Jolla, Calif., USA). Ligated DNA is packaged in vitro, using the GIGAPACK III XL packaging extract (Stratagene, La Jolla, Calif., USA). *E. coli* BL21(DE3) is transfected with the packaging mix, and colonies are selected on solid M9 medium containing L-arabinonate as the sole source of carbon for growth. Restriction enzyme mapping of three cosmids isolated from three colonies that grew on L-arabinonate indicated a common 5.0-kb DNA fragment. Further subcloning guided by assaying for L-arabinonate dehydratase activity is employed to minimize the size of the DNA fragment containing the aadh gene.

An open reading frame possessing high homology to a sugar transport protein is identified in the 5.0-kb DNA fragment employing BLAST (Basic Local Alignment Search Tool) program on the NCBI (National Center for Biotechnology Information) search engine. To further determine the function of this putative transport protein, plasmids pWN6.086A and pWN6.126A are constructed. Both plasmids contain genes encoding L-arabinonate dehydratase and benzoylformate decarboxylase, while plasmid pWN6.126A also contains the gene encoding the putative transport protein. Single colonies of *E. coli* BL21(DE3)/pWN6.086A and *E. coli* BL21(DE3)/pWN6.126A are inoculated into 5 mL LB medium containing Ap and cultured at 37° C. with agitation at 250 rpm. When the OD600 of cell cultures reached 0.4-0.6, IPTG is added (t=0) to a final concentration of 0.5 mM along with 0.5 mL of L-arabinonate (1 M). During the subsequent 36 h of cultivation, samples (1 mL) of each cell culture are removed at 12 h time intervals. Solute concentrations in culture media are determined by $^1H$ NMR. The concentration of L-arabinonate decreased in the culture medium of *E. coli* BL21(DE3)/pWN6.126A, while the concentration of L-arabinonate remained unchanged during the initial 24 h of culturing *E. coli* BL21(DE3)/pWN6.086A. Formation of 1,2,4-butanetriol is detected in the culture medium of *E. coli* BL21(DE3)/pWN6.126A at 24 h. It reached a concentration of 4.5 mM at 36 h. A decrease of the concentration of L-arabinonate was observed at 36 h in the culture medium of BL21(DE3)/pWN6.086A, but no formation of 1,2,4-butanetriol is detected. The results indicated that expression of the putative transport protein enables *E. coli* BL21(DE3)/pWN6.126A to transport L-arabinonate and produce 1,2,4-butanetriol. The S3 open reading frame encoding this potential L-arabinonic acid transport protein is designated aatp.

Enzyme Assays

Cells are collected by centrifugation at 4000×g and 4° C. Harvested cells are resuspended in buffer containing Tris-HCl (50 mM, pH 8.0) and $MgCl_2$ (10 mM) for assay of D-xylonate and L-arabinonate dehydratase while harvested cells are resuspended in sodium phosphate (50 mM, pH 6.5) for assay of D,L-3-deoxy-glycero-pentulosonate decarboxylase activity. Resuspended cells are then disrupted two times using a French press (16,000 psi, 110.4 MPa). Cellular debris is removed by centrifugation at 48000 g for 20 min. Protein concentrations are determined using the Bradford dye-binding method. (Bradford, M. M. Anal. Biochem. 1976, 72, 248.) Protein assay solution can be purchased from Bio-Rad (Hercules, Calif., USA). Protein concentrations are determined by comparison to a standard curve prepared using bovine serum albumin.

D-Xylonate and L-arabinonate dehydratase can be assayed according to procedures described by Dahms. (Dahms, A. S.;

Donald, A. *Meth. Enzymol.* 1982, 90, 302.; Anderson, R. L.; Dahms, A. S. *Meth. Enzymol.* 1975, 42C, 305.) The 2-keto acids 3-deoxy-D-glycero-pentulosonate and 3-deoxy-L-glycero-pentulosonate formed during enzyme-catalyzed dehydration are measured as semicarbazone derivatives. Two solutions are prepared and incubated separately at 30° C. for 3 min. The first solution (150 μL) contained Tris-HCl (50 mM), $MgCl_2$ (10 mM) and an appropriate amount of cell lysate at pH 8.0. The second solution (25 μL) contained potassium D-xylonate or L-arabinonate (0.1 M). After the two solutions are mixed (time=0), aliquots (30 μL) are removed at timed intervals and mixed with semicarbazide reagent (200 μL), which contained 1% (w/v) of semicarbazide and 0.9% (w/v) of sodium acetate in water. Following incubation at 30° C. for 15 min, each sample is diluted to 1 mL with $H_2O$. After removing the precipitated protein by centrifugation, the absorbance of semicarbazone is measured at 250 nm. One unit of D-xylonate or L-arabinonate dehydratase activity is defined as the formation of 1 μmol of 3-deoxy-D-glycero- or 3-deoxy-L-glycero-pentulosonate per min at 30° C. A molar extinction coefficient of 10,200 $M^{-1}cm^{-1}$ (250 nm) is used for 2-keto acid semicarbazone derivatives.

D,L-3-Deoxy-glycero-pentulosonate decarboxylase is assayed by coupling the decarboxylation reaction with D,L-3,4-dihydroxybutanal-dependent oxidation of NADH catalyzed by equine liver alcohol dehydrogenase. Synthesis of D,L-3-deoxy-glyceropentulosonic acid followed a procedure described by Stoolmiller. (Stoolmiller, A. C. *Meth. Enzymol.* 1975, 41 B, 101.) The enzyme assay solution (1 mL) contains sodium phosphate (50 mM, pH 6.5), potassium D,L-3-deoxy-glyceropentulosonate (100 mM), $MgCl_2$ (10 mM), thiamine pyrophosphate (0.15 mM), NADH (0.2 mM), 500 U of equine liver alcohol dehydrogenase, and an aliquot of cell lysate. One unit of D,L-3-deoxy-glycero-pentulosonic acid decarboxylase activity is defined as the decarboxylation of 1 μmol of D,L-3-deoxy-glycero-pentulosonic acid per min at 24° C. as measured by the oxidation of NADH at 340 nm. A molar extinction coefficient of 6,220 $M^{-1}cm^{-1}$ (340 nm) is used for NADH.

General Fermentations

Fermentations employ a 2.0 L working capacity B. Braun M2 culture vessel. Utilities are supplied by a B. Braun Biostat MD (Sartorius BBI Systems, Bethlehem, Pa., USA) controlled by a DCU-3. Data acquisition utilized a Dell Optiplex GX200 personal computer (PC) equipped with B. Braun MFCS/Win software (v2.0). Temperature, pH and glucose addition are controlled with PID control loops. Dissolved oxygen (D.O.) is monitored using a Mettler-Toledo (Columbus, Ohio, USA) 12 mm S4 sterilizable $O_2$ sensor fitted with an Ingold A-type $O_2$ permeable membrane. Samples (5-10 mL) of fermentation broth are removed at 3 or 6 h intervals. Cell densities are determined by dilution of fermentation broth with water (1:100) followed by measurement of absorption at 600 nm (OD600). The remaining fermentation broth is centrifuged to obtain cell-free broth. Solute concentrations in the cell-free broth are determined by $^1$H NMR or GC analysis. Prior to purification of microbe-synthesized D-xylonate, purification of microbe synthesized L-arabinonate, and analysis of the enantiomeric purity of microbe-synthesized D- and L-1,2,4-butanetriol, fermentation broth is centrifuged at 14000 g for 20 min and the cells are discarded. Color and protein are removed from the resulting supernatant by addition of Darco KB-B (Bennett, Colo., USA) activated carbon (20 g/L) followed by agitation at 250 rpm for 2 h. After filtration to remove activated carbon, the filtrate is treated with activated carbon a second time in the same fashion.

Microbial Oxidation of Pentoses

For microbial oxidation of D-xylose or L-arabinose, fermentation medium (1 L) contains $K_2HPO_4$ (2 g), $KH_2PO_4$ (1 g), $(NH4)_2SO_4$ (5 g) and yeast extract (5 g). Solutions of D-xylose (100 g) or L-arabinose (100 g) and $MgSO_4$ (0.24 g) are autoclaved separately and added immediately prior to initiation of the fermentation. Inoculants are started by introduction of a *Pseudomonas fragi* single colony picked from a nutrient agar plate into 5 mL of fermentation medium. Cultures are grown at 30° C. with agitation at 250 rpm until they are turbid (~24 h) and subsequently transferred to 100 mL of fermentation medium. Cultures are grown at 30° C. and 250 rpm for an additional 12 h. The inoculant (OD600=1.0-3.0) is then transferred into the fermentation vessel and the batch fermentation is initiated (t=0 h). The fermentation control settings are: 30° C., stirring speed at 650 rpm, and airflow at 0.5 L/L/min. The culture medium is maintained at pH 6.4 by addition of 2 N $H_2SO_4$ and a base solution, which is 30% $CaCO_3$ for oxidation of D-xylose or concentrated $NH_4OH$ for oxidation of L-arabinose. A standard curve is determined for each metabolite using solutions of authentic, chemically synthesized samples. (Moore, S.; Link, K. P. *J. Biol. Chem.* 1940, 133, 293.) Compounds are quantified by $^1$H NMR using the following resonances: D-xylonic acid (δ4.08, d, 1H); L-arabinonic acid (δ4.24, d, 1H); and L-arabino-1,4-lactone (δ4.64, d, 1H). A modified procedure by Buchert is employed for the purification of D-xylonate. Following treatment with activated carbon and concentration (1-1.1 L to 250 mL) of D-xylonate containing fermentation broth, EtOH (3:1, v/v) is added. After 12 h at 4° C., the precipitated calcium xylonate is filtered and dried under vacuum (95% recovery based on D-xylonate in the crude fermentation broth). Potassium D-xylonate is obtained by passing an aqueous solution of calcium xylonate through a Dowex 50 ($K^+$ form) column (Applied Membranes, Vista, Calif., USA).

After treatment with activated carbon and concentration (1-1.1 L to 100 mL) of fermentation broth resulting from microbial oxidation of L-arabinose, the solution is adjusted to pH 12.0 by addition of solid KOH for hydrolysis of the L-arabino-1,4-lactone (i.e. L-arabinono-1,4-lactone). The hydrolysis reaction is carried out at room temperature overnight. Following neutralization of the hydrolysis solution with concentrated HCl addition, a 5:1 (v/v) amount of MeOH is added relative to the L-arabinonate solution. After 12 h at 4° C., precipitated potassium L-arabinonate is filtered and dried under vacuum (92% recovery based on L-arabinonate and L-arabino-1,4-lactone in the crude fermentation broth).

Microbial Synthesis of 1,2,4-Butanetriol

For microbial synthesis of D- or L-1,2,4-butanetriol, the fermentation medium (1 L) contains Bacto tryptone (20 g), Bacto yeast extract (10 g) and NaCl (5 g). Solutions of $K_2HPO_4$ (3.75 g), glucose, and $MgSO_4$ (0.24 g) are autoclaved separately and added prior to initiation of the fermentation. Thiamine hydrochloride (0.34 g) and kanamycin (0.1 g) are added into the culture medium at the same time. Inoculants are started by introduction of a single colony picked from an agar plate into 5 mL of LB-glucose medium containing kanamycin. Cultures are grown at 37° C. with agitation at 250 rpm until they are turbid. A 0.5 mL of this culture is subsequently transferred to 100 mL of LB-glucose medium containing kanamycin, which is grown at 37° C. and 250 rpm for an additional 10 h. The inoculant (OD600=1.0-3.0) is then transferred into the fermentation vessel and the batch fermentation is initiated (t=0 h). The fermentation control settings are: 33° C., dissolved oxygen (D.O.) at 20% of air saturation, and pH 7.0. Addition of concentrated $NH_4OH$ or 2 N $H_2SO_4$ is employed to maintain pH. The initial glucose concentration in the fermentation media ranged from 15-22 g/L.

Maintenance of D.O. at 20% of air saturation proceeds through three stages during the fermentations. Stage 1 begins with an airflow setting of 0.06 L/L/min. The D.O. concentration is maintained during Stage 1 by increasing the impeller speed from its initial set point of 50 rpm to its preset maximum of 1100 rpm.

Stage 2 begins with the impeller rate at 1100 rpm D.O is then maintained at 20% of air saturation during Stage 2 by use of the mass flow controller to increase the airflow rate from 0.06 L/L/min to a preset maximum of 1.0 L/L/min. At constant impeller speed and constant airflow rate, the D.O. concentration is maintained at 20% of air saturation during Stage 3 by $O_2$ sensor-controlled glucose feeding. At the beginning of Stage 3, the D.O. concentration fell below 20% of air saturation due to residual glucose in the media. This lasted for approximately 10-30 min before glucose (65% w/v) feeding commenced. The glucose feed PID control parameters are set to 0.0 s (off) for the derivative control ($\tau_D$) and 999.9 s (minimum control action) for the integral control ($\tau_I$). $X_P$ is set to 950% to achieve a Kc of 0.1. IPTG stock solution (1 mL), and D-xylonate or L-arabinonate solution is added to the culture media upon initiation of Stage 3. The concentration of 1,2,4-butanetriol is determined by GC analysis.

Enantiomeric Purity Analysis of Microbial Synthesized 1,2,4-Butanetriol

Following concentration of partially purified 1,2,4-butanetriol fermentation broth (200 mL) to 20 mL, the solution is eluted through a Dowex 1×8-400 (OH– form) column with water. The eluant is neutralized by addition of Dowex 50 (H+ form) resin. After removing the resin by filtration, the filtrate is concentrated under vacuum. To 1,2,4-butanetriol (0.0027 g) in pyridine (0.2 mL), $CH_2Cl_2$ (0.3 mL), 4-(dimethylamino) pyridine (0.005 g), and (S)-(+)-α-methoxy-α-(trifluoromethyl) phenylacetyl chloride (0.026 g) are sequentially added. The mixture is stirred at room temperature overnight and passed through a disposable pipette containing silica gel, which is eluted with 3 mL of $CH_2Cl_2$. After removing $CH_2Cl_2$ under vacuum, the residue is redissolved in $CH_2Cl_2$ and washed with 1% $NaHCO_3$ (5 mL) and $H_2O$ (2×5 mL). The $CH_2Cl_2$ layer is concentrated under vacuum to give the Mosher ester. The Mosher esters of D- and L-1,2,4-butanetriol are analyzed employing an Agilent 1100 (Palo Alto, Calif., USA) HPLC equipped with a Chiralpak AD column (Daicel Chemical, Fort Lee, N.J., USA, 4.6 mm×250 mm), which had been equilibrated with hexane:2-propanol=98:2 (v/v). The column is eluted with the same solvent mixture at a rate of 1.25 S6 mL/min, while the eluant is monitored at 260 nm. The retention time of D- and L-1,2,4-butanetriol Mosher ester are 14.4 min and 8.1 min, respectively. Mixtures containing varying amounts of authentic D- and L-1,2,4-butanetriol are derivatized using Mosher's reagent and analyzed by HPLC. A calibration curve is generated by plotting the ratios of integrated peak areas of eluted Mosher esters prepared from mixtures of authentic D- and L-1,2,4-butanetriol against the weight ratio of D- and L-1,2,4-butanetriol in these samples. Based on this calibration curve, the percent enantiomeric excess of microbe-synthesized D- and L-1,2,4-butanetriol were determined to be 99% and >99%, respectively.

EXAMPLE 1

Fermentor-controlled cultivation (1 L) of *E. coli* DH5α/ pWN6.186A at ambient pressures and 33° C. resulted in the conversion of D-xylonic acid (10 g/L) into D-1,2,4-butanetriol (1.6 g/L) in 25% yield. Similar cultivation of *E. coli* BL21(DE3)/pWN6.222A leads to the conversion of L-arabinonic acid (10 g/L) into L-1,2,4-butanetriol (2.4 g/L) in 35% yield. Stereochemical assignments for microbe-synthesized produces are based on the conversion to Mosher esters and comparison with similarly derivatized D- and L-1,2,4-butanetriol obtained from commercial sources. (Dale, J. A.; Mosher, H. S. *J. Am. Chem. Soc.* 1973, 95, 51.2.) *E. coli* DH5α/pWN6.186A synthesized ethylene glycol (0.093 g/L) for a 3% yield of this byproduct, while *E. coli* BL21(DE3)/ pWN6.222A synthesized ethylene glycol (0.087 g/L) in 2% yield.

EXAMPLE 2

Microbial synthesis begins with pentose oxidation using fermentor-controlled cultures (e.g., 1 L scale) of *Pseudomonas fragi* ATCC4973. (Buchert, J.; Viikari, L.; Linko, M.; Markkanen, P. *Biotechnol. Lett.* 1986, 8, 541. and Weimberg, R. *J. Bio. Chem.* 1961, 236, 629). D-xylose (100 g/L) is oxidized at 30° C. to D-xylonic acid and produces a 70% yield (77 g/L). L-arabinose is similarly oxidized and produces a 54% overall yield to a mixture of L-arabino-1,4-lactone (40 g/L) and L-arabinonic acid (15 g/L). The lactone is subsequently hydrolyzed to L-arabinonic acid. *Escherichia coli* constructs are then employed for the conversion of D-xylonic acid and L-arabinonic acid into the respective enantiomers of 1,2,4-butanetriol.

What is claimed is:

1. A process for making 1,2,4-butanetriol, comprising the steps of
   (a) converting D-xylose to D-xylonic acid by contacting the D-xylose with a D-xylose dehydrogenase enzyme derived from *Pseudomonas*;
   (b) converting the D-xylonic acid from step (a) to 3-deoxy-glycero-pentulosonic acid by contacting the D-xylonic acid with a D-xylonate dehydratase enzyme derived from *Escherichia*;
   (c) converting 3-deoxy-glycero-pentulosonic acid from step (b) to 3,4-dihydroxybutanal by contacting the 3-deoxy-glycero-pentulosonic acid with a benzylformate decarboxylase enzyme derived from *Pseudomonas, Erwina, Acetobacter, Zymobacter*, or *Sacchararomyces*; and
   (d) converting 3,4-dihydroxybutanal from step (c) to 1,2, 4-butanetriol by contacting the 3,4-dihydroxybutanal with a dehydrogenase enzyme derived from an *Escherichia*.

2. The process according to claim 1, wherein step (b) converts D-xylonic acid to D-3-deoxy-glycero-pentulosonic acid, step (c) converts D-3-deoxyglycero-pentulosonic acid to D-3,4-dihydroxybutanal, and step (d) converts D-3,4-dihydroxybutanal to D-1,2,4-butanetriol.

3. The process according to claim 1, the process involving producing D-1,2,4-butanetriol from D-xylonic acid, wherein the process comprises the steps of:
 (a) providing
  (1) D-xylonic acid, and
  (2) a recombinant cell capable of performing uptake of D-xylonic acid, and containing nucleic acid from which the cell can express (a) at least one D-xylonate dehydratase, (b) at least one 2-ketoacid decarboxylase, and (c) at least one alcohol dehydrogenase or carbonyl reductase,
 (b) contacting said cell with said D-xylonic acid under conditions in which the cell uptakes D-xylonic acid and in which the cell expresses, from said nucleic acid, the D-xylonate dehydratase, 2-ketoacid decarboxylase, and alcohol dehydrogenase or carbonyl reductase, whereupon said cell
 (c) converts said D-xylonic acid to D-3-deoxy-glycero-pentulosonic acid using the D-xylonate dehydratase;
 (d) converts said D-3-deoxy-glycero-pentulosonic acid to D-3,4-dihydroxybutanal using the 2-ketoacid decarboxylase; and
 (e) converts said D-3,4-dihydroxybutanal to D-1,2,4-butanetriol using the alcohol dehydrogenase or carbonyl reductase,
 thereby producing D-1,2,4-butanetriol.

4. The process according to claim 1, the process involving producing D-1,2,4-butanetriol from D-xylose, wherein the process comprises the steps of:
 (a) providing
  (1) D-xylose, and
  (2) a recombinant cell capable of performing uptake of D-xylose, and containing nucleic acid from which the cell can express: (a) at least one D-xylose dehydrogenase, or at least one D-xylose dehydrogenase and at least one D-xylonolactonase; (b) at least one D-xylonate dehydratase; (c) at least one 2-ketoacid decarboxylase; and (d) at least one alcohol dehydrogenase or carbonyl reductase,
 (b) contacting said cell with said D-xylose under conditions in which the cell uptakes D-xylose and in which the cell expresses, from said nucleic acid: the D-xylose dehydrogenase and, optionally, the D-xylonolactonase; the D-xylonate dehydratase; the 2-ketoacid decarboxylase; and the alcohol dehydrogenase or carbonyl reductase,
 whereupon said cell
 (c) converts D-xylose to D-xylonic acid using the D-xylose dehydrogenase, either alone or in combination with the D-xylonolactonase;
 (d) converts said D-xylonic acid to D-3-deoxy-glycero-pentulosonic acid using the D-xylonate dehydratase;
 (e) converts said D-3-deoxy-glycero-pentulosonic acid to D-3,4-dihydroxybutanal using the 2-ketoacid decarboxylase; and
 (f) converts said D-3,4-dihydroxybutanal to D-1,2,4-butanetriol using the alcohol dehydrogenase or carbonyl reductase,
 thereby producing D-1,2,4-butanetriol.

5. The process according to claim 1, wherein said process proceeds according to the reaction scheme from 4a to 5a to 6a to 7a to 1a:

6. The process according to claim 1, wherein said process is performed in a transformed cell.

7. The process according to claim 1, wherein said process is performed in a transformed microbial cell.

8. The process according to claim 1, wherein said process is performed in an *E. coli* transformant.

9. The process according to claim 1, wherein said process is performed in anyone of host organism *E. coli* DR 5 which is transformed with plasmid pWN6.186A or host organism *E. coli* BL21(DE3) which is transformed with plasmid pWN6.222A.

10. The process according to claim 7, wherein said process comprises culturing the transformed microbial cell in a medium containing at least one of D-xylonic acid, L-arabinonic acid, D-xylose, or L-arabinose.

11. The process according to claim 10, further comprising growing the culture with agitation until said cultures appeared turbid.

12. The process according to claim 11, further comprising, transferring the turbid culture to a fermentation medium containing an antibiotic and growing said culture until it reaches OD600 of about 1.0 to about 3.0.

13. The process according to claim 12, further comprising transferring the turbid culture as combined with the antibiotic into the fermentation medium, thereby initiating fermentation.

14. The process according to claim 13, further comprising maintaining a dissolved oxygen content of about 20% of air saturation through a plurality of stages of the fermentation.

15. The process according to claim 1, wherein said process additionally comprises isolating 1,2,4-butanetriol resulting from step (d).

16. A process for making 3,4-dihydroxybutanal, comprising culturing a microbe expressing 2-ketoacid decarboxylase enzyme derived from *Pseudomonas, Erwina, Acetobacter, Zymobacter*, or *Sacchararomyces* in the presence of 3-deoxyglycero-pentulosonic acid, thereby converting 3-deoxy-glycero-pentulosonic acid to 3,4-dihydroxybutanal by contacting the 3-deoxy-glycero-pentulosonic acid with the 2-ketoacid decarboxylase.

17. The process according to claim 16, wherein said process comprises the steps of:
(a) converting D-xylose to D-xylonic acid;
(b) converting acid resulting from step (a) to 3-deoxyglycero-pentulosonic acid; and
(c) converting 3-deoxy-glycero-pentulosonic acid resulting from step (b) to 3,4-dihydroxybutanal.

18. The process according to claim 17, wherein step (b) converts D-xylonic acid to D-3-deoxy-glycero-pentulosonic acid, and step (c) converts D-3deoxy-glycero-pentulosonic acid to D-3,4-dihydroxybutanal.

19. The process according to claim 17, wherein said process comprises contacting, with D-xylonic acid, a recombinant cell that is capable of performing uptake of D-xylonic acid, and that expresses at least one D-xylonate dehydratase and at least one 2-ketoacid decarboxylase.

20. The process according to claim 17, wherein said process comprises contacting, with D-xylose a recombinant cell that is capable of performing uptake of D-xylose and expresses
(a1) at least one D-xylose dehydrogenase, or at least one D-xylose dehydrogenase and at least one D-xylonolactonase, (b1) at least one D-xylonate dehydratase, and (c1) at least one 2-ketoacid decarboxylase.

21. The process according to claim 17, wherein said process is performed in a transformed cell.

22. The process according to claim 17, wherein said process is performed in a transformed microbial cell.

23. The process according to claim 17, wherein said process is performed in an *E. coli* transformant.

24. The process according to claim 22, wherein said process comprises culturing the transformed microbial cell in a medium containing at least one of D-xylonic acid, L-arabinonic acid, D-xylose, or L-arabinose.

25. The process according to claim 24, further comprising growing the culture with agitation until said culture appears turbid.

26. The process according to claim 25, further comprising, transferring the turbid culture to a fermentation medium containing an antibiotic and growing said culture until it reaches OD600 of about 1.0 to about 3.0.

27. The process according to claim 26, further comprising transferring the turbid culture as combined with the antibiotic into the fermentation medium, thereby initiating fermentation.

28. The process according to claim 27, further comprising maintaining a dissolved oxygen content of about 20% of air saturation through a plurality of stages of the fermentation.

29. The process according to claim 17, wherein said process additionally comprises isolating 3,4-dihydroxybutanal resulting from step (c).

30. The process according to claim 1, wherein converting D-xylose to D-xylonic acid is enzymatically catalyzed using an EC 1.1.1.175 D-xylose dehydrogenase, an EC 1.1.1.179 NADP-dependent D-xylose dehydrogenase, or a combination thereof.

31. The process according to claim 30, wherein the EC 1.1.1.175 D-xylose dehydrogenase, an EC 1.1.1.179 NADP-dependent D-xylose dehydrogenase are from *Pseudomonas fragi*.

32. The process according to claim 1, wherein converting D-xylonic acid from step (a) to 3-deoxy-glycero-pentulosonic acid includes catalyzing the conversion of D-xylonic acid from step (a) to 3-deoxy-glycero-pentulosonic acid using an EC 4.2.1.82 D-xylonate dehydratase.

33. The process according to claim 32, wherein the EC 4.2.1.82 D-xylonate dehydratase is from *Escherichia coli*.

34. The process according to claim 1, wherein the converting 3-deoxy-glycero-pentulosonic acid from step (b) to 3,4-dihydroxybutanal is enzymatically catalyzed using an EC 4.1.1.1 pyruvate decarboxylase, an EC 4.1.1.7 benzoylformate decarboxylase, an EC 4.1.1.74 indole 3-pyruvate decarboxylase, or a combination thereof.

35. The process according to claim 34, wherein the EC 4.1.1.1 pyruvate decarboxylase is from *Zymomonas mobilis, Acetobacter pasteurianus, Zymobacter palmae*, or *Saccharomyces cerevisiae*, the EC 4.1.1.7 benzoylformate decarboxylase is from *Pseudomonas putida*, and the EC 4.1.1.74 indole 3-pyruvate decarboxylase is from *Erwinia herbicola*.

36. The process according to claim 1, wherein the converting 3,4-dihydroxybutanal from step (c) to 1,2,4-butanetriol is enzymatically catalyzed using an EC 1.1.1.1 NADH-dependent alcohol dehydrogenase, an EC 1.1.1.2 NADPH-dependent alcohol dehydrogenase, an EC 1.1.1.184 NADPH-dependent carbonyl reductase, or a combination thereof.

37. The process according to claim 36, wherein the EC 1.1.1.1 NADH-dependent alcohol dehydrogenase, the EC 1.1.1.2 NADPH-dependent alcohol dehydrogenase, and the EC 1.1.1.184 NADPH-dependent carbonyl reductase are from *Escherichia coli*.

38. The process of claim 1 wherein:
the D-xylose dehydrogenase enzyme is derived from *Pseudomonas fragi* and expressed in *Pseudomonas putida* or *Escherichia coli;*
the D-xylonate dehydratase enzyme is derived from *Escherichia coli* and expressed in *Escherichia coli;*
the decarboxylase enzyme is derived from a *Pseudomonas putida* and expressed in *Escherichia coli;* and
the dehydrogenase enzyme derived *Escherichia coli* and expressed in *Escherichia coli*.

39. The process of claim 16 wherein:
the decarboxylase enzyme is derived from a *Pseudomonas putida* and expressed in *Escherichia coli*.

* * * * *